(12) United States Patent
Sorsak

(10) Patent No.: US 7,074,940 B2
(45) Date of Patent: Jul. 11, 2006

(54) PREPARATION OF PHARMACEUTICALLY ACCEPTABLE ATORVASTATIN SALTS IN NON-CRYSTALLINE FORMS

(75) Inventor: Gorazd Sorsak, Kidricevo (SI)

(73) Assignee: Lek Pharmaceutical & Chemical Co. d.d., Ljubljana (SI)

( * ) Notice: Subject to any disclaimer, the term of this patent is extended or adjusted under 35 U.S.C. 154(b) by 446 days.

(21) Appl. No.: 10/677,344

(22) Filed: Oct. 3, 2003

(65) Prior Publication Data

US 2004/0072895 A1    Apr. 15, 2004

Related U.S. Application Data

(60) Division of application No. 10/323,444, filed on Dec. 18, 2002, now Pat. No. 6,750,353, which is a continuation-in-part of application No. PCT/IB02/00161, filed on Jan. 22, 2002.

(30) Foreign Application Priority Data

Jan. 23, 2001    (SI)    .............................. P-01100010

(51) Int. Cl.
 *C07D 207/355* (2006.01)
(52) U.S. Cl. ................................... 548/537
(58) Field of Classification Search ................. 548/537
See application file for complete search history.

(56) References Cited

U.S. PATENT DOCUMENTS

| | | | |
|---|---|---|---|
| 4,681,893 A | 7/1987 | Roth |
| 5,003,080 A | 3/1991 | Butler et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,273,995 A | 12/1993 | Roth |
| 5,280,126 A | 1/1994 | Butler et al. |
| 5,298,627 A | 3/1994 | Butler et al. |
| 5,342,952 A | 8/1994 | Butler et al. |
| 5,397,792 A | 3/1995 | Butler et al. |
| 5,969,156 A | 10/1999 | Briggs et al. |
| 6,087,511 A | 7/2000 | Lin et al. |
| 6,121,461 A | 9/2000 | McKenzie |
| 6,274,740 B1 | 8/2001 | Lin et al. |

FOREIGN PATENT DOCUMENTS

| | | |
|---|---|---|
| EP | 0 330 172 | 8/1989 |
| WO | WO 94/20492 | 9/1994 |
| WO | WO 97/03958 | 2/1997 |
| WO | WO 97/03959 | 2/1997 |
| WO | WO 97/03960 | 2/1997 |
| WO | WO 00/71116 | 11/2000 |

OTHER PUBLICATIONS

Baumann et al., "The convergent synthesis of CI-981, an optically active, highly potent, tissue selective inhibitor of HMG-CoA reductase", Tetrahedron Letters, 33(17), 2283-2284 (1992).

Konno et al., "Physical and chemical changes of medicinals in mixtures with absorbents in the solid state. IV.1) Study on reduced-pressure mixing for practical use of amorphous mixtures of flufenamic acid", Chem. Pharm. Bull., 38(7), 2003-2007 (1990).

*Primary Examiner*—Kamal A. Saeed
(74) *Attorney, Agent, or Firm*—Heller Ehrman LLP

(57)    ABSTRACT

Non-crystalline, in particular amorphous, pharmaceutically acceptable atorvastatin salts, especially the calcium salt, are prepared from atorvastatin lactone or from a compound of formula (I)

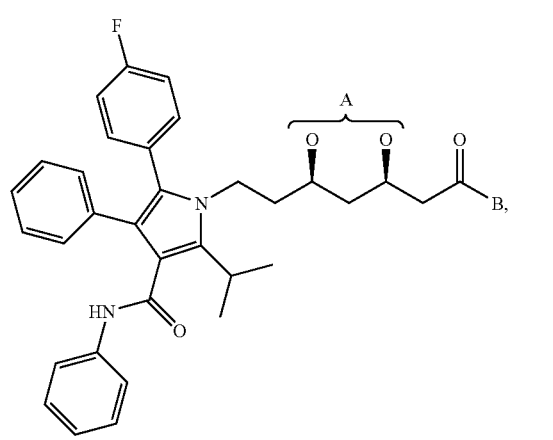

where A denotes a common protecting group or separate protecting groups for the two hydroxy groups, and B denotes a carboxylic acid protecting group, without the need of prior formation of atorvastatin lactone, the crystalline form of the atorvastatin salt, or a mixture of amorphous and crystalline forms of the atorvastatin salt. Pharmaceutical formulations are prepared from these salts.

19 Claims, 1 Drawing Sheet

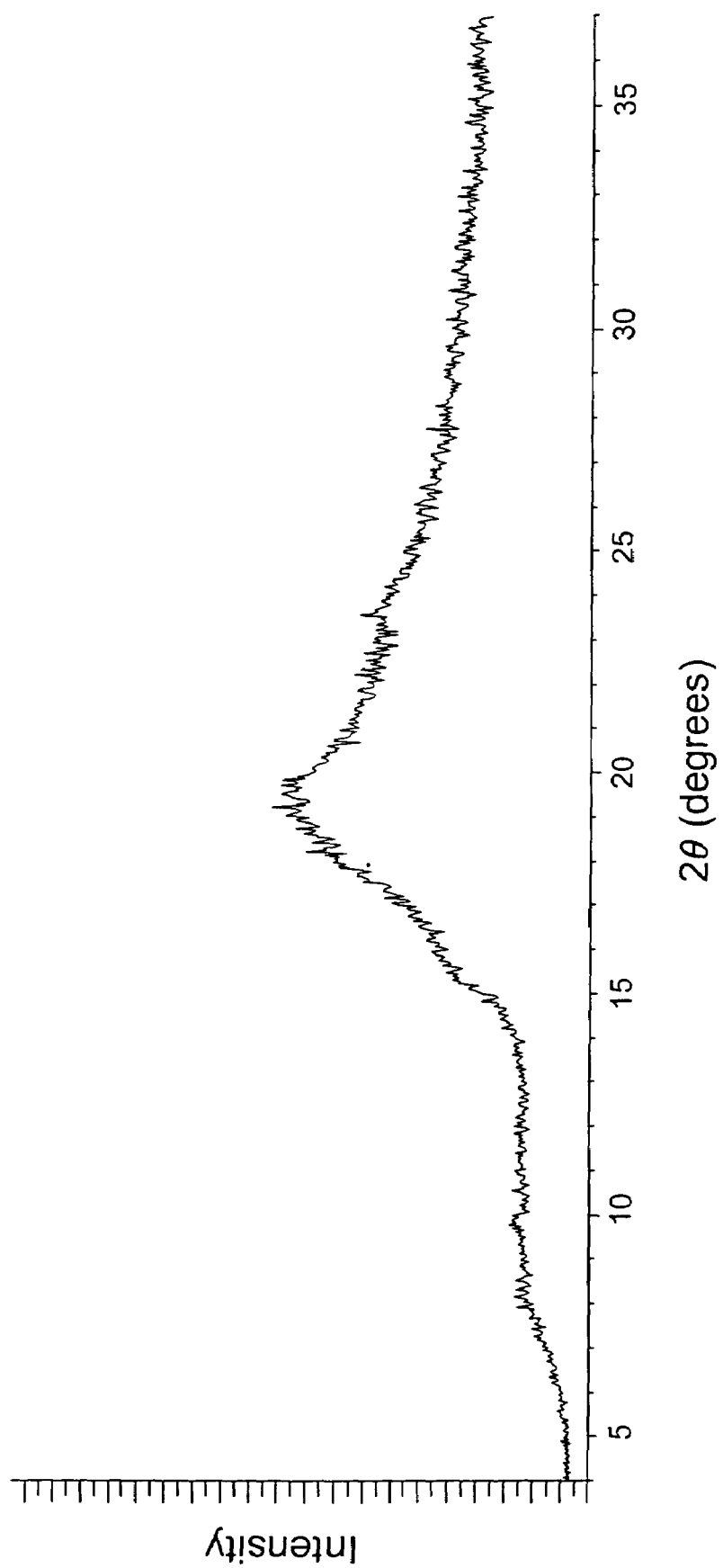

PREPARATION OF PHARMACEUTICALLY ACCEPTABLE ATORVASTATIN SALTS IN NON-CRYSTALLINE FORMS

CROSS-REFERENCE TO RELATED APPLICATIONS

This application is a divisional of application Ser. No. 10/323,444, filed Dec. 18, 2002 now U.S. Pat. No. 6,750,353. Application Ser. No. 10/323,444 is a continuation-in-part of International application Ser. No. PCT/IB02/00161, filed Jan. 22, 2002 and designating the United States. International application Ser. No. PCT/IB02/00161 claims the priority of Slovenian application No. P-01100010, filed Jan. 23, 2001. Each of these applications is incorporated into this application by reference.

BACKGROUND OF THE INVENTION

1. Field of the Invention

This invention relates to a method of preparing pharmaceutically acceptable atorvastatin salts in noncrystalline form.

2. Description of the Related Art

Atorvastatin calcium (USAN: the INN for the salt is atorvastatin), the substance having the chemical name [(R—(R*,R*)]-2-(4-fluorophenyl)-β,δ-dihydroxy-5-(1-methylethyl)-3-phenyl-4-(phenylamino)carbonyl-1H-pyrrole-1-heptanoic acid calcium salt (2:1) and the formula

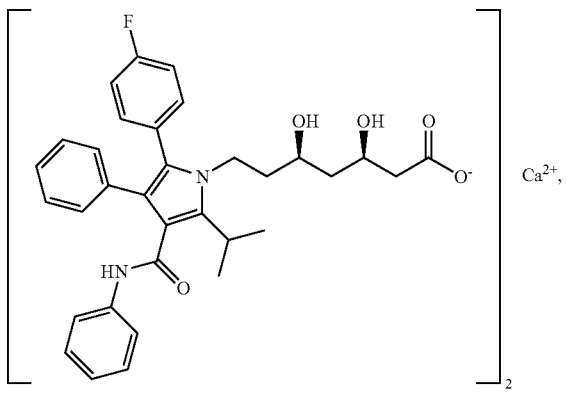

is known as an HMG-CoA reductase inhibitor and is used as an antihypercholesterolemic agent.

Atorvastatin lactone is the compound of the formula

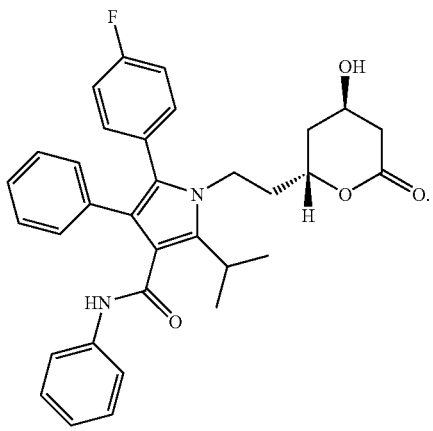

Processes for the preparation of atorvastatin and its salts, atorvastatin lactone, and key intermediates, are disclosed in U.S. Pat. Nos. 5,003,080; 5,097,045; 5,103,024; 5,124,482; 5,149,837; 5,155,251; 5,216,174; 5,245,047; 5,248,793; 5,280,126; 5,342,952; and 5,397,792. Atorvastatin is usually prepared as the calcium salt since this enables atorvastatin to be conveniently formulated in pharmaceutical formulations, for example, in tablets, capsules, powders and the like for oral administration.

Atorvastatin calcium can exist in amorphous form or in one of several crystalline forms (Form I, Form II, Form III and Form IV), which are disclosed in International Publications Nos. WO 97/3958 (U.S. Pat. No. 6,121,461) and WO 97/3959 (U.S. Pat. No. 5,969,156). It is known that the amorphous forms of a number of pharmaceutical substances exhibit different dissolution characteristics and bioavailability patterns compared to the crystalline forms (Konno T., *Chem. Pharm. Bull.*, 1990, 38:2003–2007). For some therapeutic indications the bioavailability is one of the key parameters determining the form of the substance to be used in a pharmaceutical formulation. Since processes for the crystallization and the preparation, respectively, of the amorphous substance are sometimes difficult, and sometimes afford amorphous-crystalline mixtures, that is, a crystalline form instead of an amorphous form, there is a constant need for processes which enable the preparation of a non-crystalline form without simultaneous formulation of crystalline forms, that is, which will enable the conversion of the crystalline form into the non-crystalline form.

Atorvastatin calcium is a substance which is very slightly water-soluble, and it has been found that the crystalline forms are less readily soluble than the amorphous form, which may cause problems in the bioavailability of atorvastatin in the body. It has been found that the production of amorphous atorvastatin calcium according to the previously disclosed processes was not consistently reproducible, and therefore a process has been developed for converting the crystalline forms of atorvastatin calcium (formed in the synthesis of atorvastatin) to the amorphous form. The process is described in International Publication No. WO 97/3960 (U.S. Pat. No. 6,087,511) and comprises dissolving a crystalline form of atorvastatin calcium in a non-hydroxylic solvent and removing the solvent to afford amorphous atorvastatin calcium. The preferred non-hydroxylic solvent is selected from the group consisting of tetrahydrofuran and a mixture of tetrahydrofuran and toluene.

The disadvantage of the above process is primarily use of non-nature-friendly solvents. A similar process is described in International Publication No. WO 00/71116 and comprises dissolving the crystalline form of atorvastatin calcium in a non-hydroxylic solvent, such as, for example, tetrahydrofuran. To the solution of atorvastatin calcium is added a nonpolar organic solvent, or the solution of atorvastatin calcium is added to a nonpolar organic solvent, to allow atorvastatin calcium to precipitate. The formed precipitate is filtered off.

Synthesis of amorphous atorvastatin calcium is demanding and accordingly the cost of the finished product is high.

SUMMARY OF THE INVENTION

It is an object of this invention to minimize the number of synthesis steps in the process for the preparation of pharmaceutically acceptable atorvastatin salts in non-crystalline form and in this manner to improve the yield.

The present invention provides a process for the conversion of a compound of formula (I)

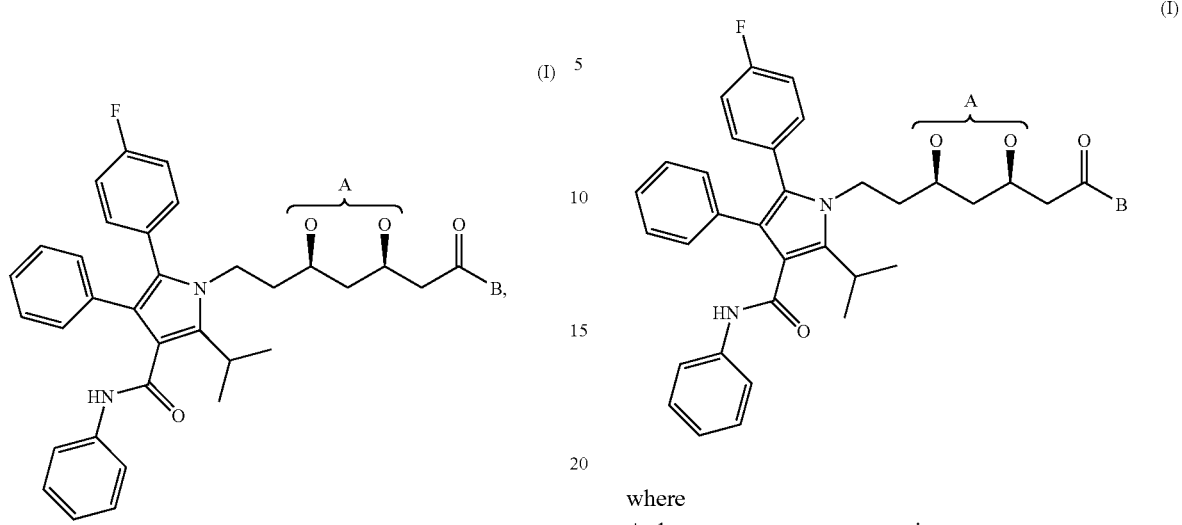

where A denotes a common protecting group or separate protecting groups for the two hydroxy groups, and B denotes a carboxylic acid protecting group, into a non-crystalline, in particular amorphous, pharmaceutically acceptable atorvastatin salt, especially the calcium salt, without the need of prior formation of atorvastatin lactone, the crystalline form of the atorvastatin salt, or a mixture of amorphous and crystalline forms of the atorvastatin salt.

In a further aspect, the present invention also provides the conversion of atorvastatin lactone into a non-crystalline, in particular amorphous, pharmaceutically acceptable atorvastatin salt without intermediate formation of the atorvastatin salt in crystalline form or a mixture of amorphous and crystalline forms.

In a still further aspect, the present invention also provides a process for the preparation of a pharmaceutical formulation containing a pharmaceutically acceptable atorvastatin salt, especially the calcium salt, which has been prepared directly in the non-crystalline, in particular in the amorphous, form.

BRIEF DESCRIPTION OF THE FIGURE

The FIGURE shows an X-ray powder diffractogram of atorvastatin calcium obtained by the process of this invention.

DETAILED DESCRIPTION OF THE INVENTION

Accordingly, the present invention in the first aspect provides a process for preparing a pharmaceutically acceptable atorvastatin salt in non-crystalline form, which comprises:
a) providing a solution in a non-hydroxylic solvent of a compound of formula (I)

where
A denotes a common protecting group or separate protecting groups for the two hydroxy groups, and
B denotes a carboxylic acid protecting group;
b) deprotecting the two hydroxy groups;
c) deprotecting the carboxylic acid group; where steps b) and c) may be performed in either order;
d) optionally concentrating the solution to not more than half its initial volume;
e) adding water to the optionally concentrated solution;
f) adding a solvent which is slightly miscible or immiscible with water and in which the pharmaceutically acceptable atorvastatin salt is insoluble or practically insoluble, in an amount not less than the water volume added in step e);
g) optionally mixing the phases, and then separating the two phases;
h) neutralizing the aqueous phase;
i) converting atorvastatin in the aqueous phase to the pharmaceutically acceptable salt; and
j) precipitating the pharmaceutically acceptable atorvastatin salt in non-crystalline form.

The compound of formula (I) is preferably a compound of formula (II)

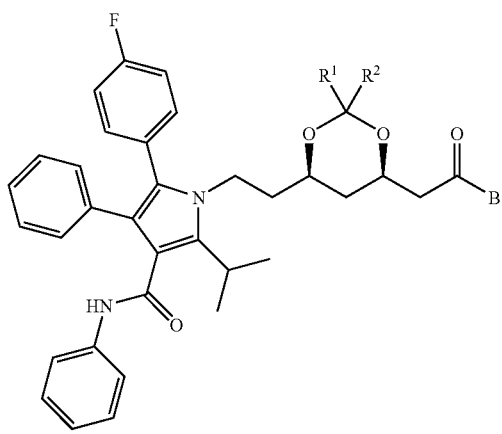

where

R$^1$ and R$^2$ are independently hydrogen, alkyl of from one to three carbon atoms, or phenyl, or R$^1$ and R$^2$ together form an alkylene of four or five carbon atoms, and B is a) OR$^3$ where R$^3$ is straight or branched chain alkyl of from one to eight carbon atoms, cycloalkyl of from three to six carbon atoms, or aralkyl (straight or branched chain alkyl of from one to four carbon atoms substituted with a phenyl group that is optionally substituted with up to three straight or branched chain alkyl groups of from one to four carbon atoms), preferably tert-butyl, tert-amyl, or α,α-dimethylbenzyl, or b) NR$^4$R$^5$ where R$^4$ and R$^5$ are independently straight or branched chain alkyl of from one to ten carbon atoms, cycloalkyl of from three to seven carbon atoms (such as cyclopropyl, cyclobutyl, cyclopentyl, or cyclohexyl), aryl or aralkyl (such as phenyl or benzyl), or R$^4$ and R$^5$ together form an alkylene of from four to six carbon atoms of which one or two carbon atoms may be replaced by hetero atoms (such as O), optionally substituted with one or more alkyl groups of from one to four carbon atoms, such as —(CH$_2$)$_4$—, —(CH$_2$)$_5$—, —CH(R$^6$)—(CH$_2$)$_3$—, —CH(R$^6$)—(CH$_2$)$_4$—, —CH(R$^6$)—(CH$_2$)$_2$—CH(R$^6$)—, —CH(R$^6$)—(CH$_2$)$_2$—CH(R$^6$)—, —CH$_2$CH$_2$OCH$_2$CH$_2$—, —CH(R$^6$)—CH$_2$OCH$_2$CH$_2$—, and —CH(R$^6$)—CH$_2$OCH$_2$—CH(R$^6$)—, where R$^6$ is straight or branched chain alkyl of from one to four carbon atoms.

A particular example of a compound of formula (I) is the compound of formula (III)

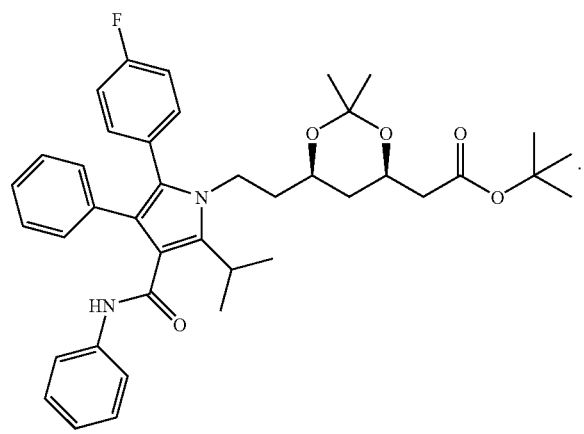

(III)

The preparation of the compounds of formulae (I), (II), and (III) is described in European Published Application No. 0 330 172 (U.S. Pat. No. 5,003,080) and International Publication No. WO 94/20492 (U.S. Pat. No. 5,298,627), these documents being incorporated herein by reference.

In the second aspect, this invention further relates to a process for the conversion of atorvastatin lactone into a pharmaceutically acceptable atorvastatin salt in non-crystalline form, which comprises providing the atorvastatin lactone in a non-hydroxylic solvent, opening the lactone ring, and then performing steps d) to j) of the first aspect of the invention are performed.

In other words, the process of the second aspect of this invention comprises:

a') providing a solution of atorvastatin lactone in a non-hydroxylic solvent;

b') opening the lactone ring;

c') optionally concentrating the solution to not more than half its initial volume;

d') adding water to the optionally concentrated solution;

e') adding a solvent which is slightly miscible or immiscible with water and in which the pharmaceutically acceptable atorvastatin salt is insoluble or practically insoluble, in an amount not less than the water volume added in step d');

f') optionally mixing the phases, and then separating the two phases;

g') neutralizing the aqueous phase;

h') converting atorvastatin in the aqueous phase to the pharmaceutically acceptable salt; and i') precipitating the pharmaceutically acceptable atorvastatin salt in non-crystalline form.

The preparation of atorvastatin lactone is also described in European Published Application No. 0 330 172 (U.S. Pat. No. 5,003,080) and International Publication No. WO 94/20492 (U.S. Pat. No. 5,298,627), these documents being incorporated herein by reference.

The present invention is described in more detail by referring to the following embodiments.

According to the process, the compound of formula (I), especially that of formula (II) and in particular that of formula (III), is provided in solution in a non-hydroxylic solvent. The solution may be provided in the course of the synthesis of the compound, or the compound may be dissolved in an appropriate amount, for example from 100 mL to 300 mL per 7 g of the compound of formula (I) (a maximum concentration of the compound of formula (I) is 80 g/L), of a non-hydroxylic solvent such as, for example, tetrahydrofuran, 1,4-dioxane, acetone, ethyl acetate or a mixture of these solvents; or mixtures of mentioned solvents with toluene, n-heptane, n-hexane, acetonitrile in the volume ratio from 1:0.01 to 1:1.0. Then, the deprotection of the two hydroxy groups in the side-chain (in the 3-and 5-positions) of the compound is performed, which can conveniently be done by the addition of an acid such as a mineral acid, for example diluted hydrochloric acid or sulfuric acid, trifluoroacetic acid, formic acid, propanoic acid, or para-toluenesulfonic acid. The molar ratio of the added acid to the compound of formula (I), (II), or (III) is from 1:0.05 to 1:0.2 (for monoprotic acids), preferably from 1:0.09 to 1:0.1. The resulting solution is kept, preferably while being mixed by stirring, agitating or shaking the solution, at a temperature of from 5° C. to 40° C., preferably at a room temperature so that the compound (1), (II) or (III), respectively, is no longer detectable by thin-layer chromatography (TLC). Then, the deprotection of the carboxylic acid group (removal of moiety B such as R$^3$, e.g., tert-butyl), is carried out, which can conveniently be done by adding an appropriate base such as an alkali metal hydroxide or alkaline earth metal hydroxide, for example sodium hydroxide, potassium hydroxide, lithium hydroxide, barium hydroxide and the like, sodium or potassium hydroxide being preferred, to the solution to adjust the pH of the solution to from 8 to 13, preferably from 9 to 12. The resulting solution is kept, preferably while being mixed by stirring, agitating or shaking the solution, at a temperature of from 5° C. to 40° C., preferably at room temperature, so that hydroxy group deprotected, carboxylic acid group protected compound is no longer detectable by thin-layer chromatography (TLC).

The solution is then optionally concentrated, for example by evaporation in vacuo, to not more than half of its initial volume, preferably from 15% to 50% of the initial volume, and more preferably to about 25% of the initial volume. The optionally concentrated solution is then diluted with water, preferably with a volume from 0.2-fold to 5-fold, e.g. from 0.6-fold to 3-fold, such as 0.6-fold to 1.5-fold, that of the volume of the optionally concentrated solution. To this solution is added a solvent which is slightly miscible or immiscible with water and in which the desired atorvastatin salt, such as atorvastatin calcium, is insoluble or practically insoluble (i.e. in which the solubility of the atorvastatin salt is not more than 0.1 mg/mL at 25° C.), using about the same or a higher volume than the previously added water volume, preferably from 1-fold to 5-fold, and more preferably 2-fold to 3-fold, of the previously added water volume. Examples of suitable solvents include hexane, heptane, cyclohexane, ether, diisopropyl ether, and the like. Preferably, the resulting solution is vigorously mixed, for example by stirring, agitating or shaking, and subsequently the phases are separated. Then, the aqueous phase is preferably rapidly stirred, agitated or shaken while an acid, e.g. a mineral acid as mentioned above such as hydrochloric acid, is carefully added to neutralize the solution, preferably adjusting the pH of the aqueous phase to from 6.5 to 8, more preferably to from 6.8 to 7.5.

Then, the atorvastatin so obtained in its dihydroxy carboxylic acid form is converted to a pharmaceutically acceptable salt form. The most preferred salt form is the calcium salt. This may be carried out by heating the resulting neutralized aqueous solution to a temperature of from 30° C. to 40° C., preferably at about 35° C. To this solution, which is rapidly mixed by stirring, agitation or shaking, is added a from 0.05M to 0.5M, preferably from 0.1M to 0.3M, aqueous solution of a salt of the desired cation, which is correspondingly preheated to from 30° C. to 40° C., preferably at about 35° C. In order to obtain the preferred calcium salt form of atorvastatin, a suitable calcium salt, preferably calcium acetate, calcium citrate, calcium oxalate, calcium chloride or calcium iodide, is used. After the completed addition, the mixture is preferably kept, suitably under a mixing operation like stirring, agitating or shaking, for a suitable period, for example for from 0.5 hour to 3 hours and preferably for about from 1 hour to 2 hours, at a temperature of from 10° C. to 30° C., preferably from 20° C. to 25° C.

Then, a precipitate of the atorvastatin salt is formed. To this end, the solution may be cooled to a lower temperature, for example to a temperature of from 2° C. to 15° C., preferably from 4° C. to 10° C. In place of cooling the solution, the atorvastatin salt, e.g. atorvastatin calcium, may also be precipitated by the addition of a water-miscible organic solvent in which the atorvastatin salt is slightly soluble or practically insoluble.

As a further alternative, the atorvastatin salt, e.g. atorvastatin calcium, may be precipitated by concentrating the solution, for example, in a vacuum evaporator.

To give the atorvastatin salt, e.g. atorvastatin calcium, in the desired non-crystalline form, the formed precipitate may be obtained by appropriate means and, thus, may be filtered, rinsed with water and dried.

In case the starting substance is atorvastatin lactone, the lactone is correspondingly provided in solution. Likewise, the solution may be provided in the course of the synthesis of the lactone, or the lactone may be dissolved in an appropriate amount, for example from 100 mL to 300 mL per 8.5 g of the lactone, of a non-hydroxylic solvent such as, for example, tetrahydrofuran.

Then, the lactone ring is opened, which is suitably done by adding a base, for example an alkali metal or alkaline earth metal hydroxide as mentioned above such as NaOH. The molar ratio of the added base to lactone is from 1:0.2 to 1:0.6, preferably from 1:0.29 to 1:0.57. The resulting solution is heated to an appropriate temperature, suitably to from 40° C. to 60° C. and preferably to about 50° C., and maintained at this temperature for a suitable period until the lactone is no longer detectable by TLC.

Subsequently, the solution is concentrated and further processed as described above for the preparation of the non-crystalline substance from compound (I) using steps d) to j) described above.

According to the third aspect of the present invention, the process for the preparation of a pharmaceutical formulation containing an atorvastatin salt, preferably atorvastatin calcium, in a non-crystalline form comprises preparing the atorvastatin salt in a non-crystalline form from either the compound of formula (I), more specifically of formulae (II) or (III), or from the lactone, and mixing the thus prepared non-crystalline atorvastatin salt with a pharmaceutically acceptable carrier in a conventional manner. Preferably, a non-crystalline atorvastatin calcium formulation is prepared. The pharmaceutical formulation is generally solid in the form of tablets, capsules, powders and the like for oral administration.

The pharmaceutical formulation thus prepared may include, in addition to the thus directly prepared pharmaceutically acceptable atorvastatin salt in non-crystalline form, in particular non-crystalline atorvastatin calcium, one or more fillers, such as microcrystalline cellulose, lactose, sugars, starches, modified starch, mannitol, sorbitol and other polyols, dextrin, dextran and maltodextrin, calcium carbonate, calcium phosphate and/or hydrogen phosphate, calcium sulfate, one or more binders, such as lactose, starches, modified starch, dextrin, dextran and maltodextrin, microcrystalline cellulose, sugars, polyethylene glycols, hydroxypropyl cellulose, hydroxypropyl methylcellulose, ethylcellulose, hydroxyethyl cellulose, methylcellulose, carboxymethyl cellulose, gelatin, acacia gum, tragacanth, polyvinylpyrrolidone, magnesium aluminum silicate, one or more disintegrating agents such as croscarmellose sodium, cross-linked polyvinylpyrrolidone, cross-linked carboxymethylstarch, starches and microcrystalline cellulose, magnesium aluminum silicate, polyacrylin potassium, one or more different glidants such as magnesium stearate, calcium stearate, zinc stearate, calcium behenate, sodium stearyl fumarate, talc, magnesium trisilicate, stearic acid, palmitic acid, carnauba wax, silicon dioxide, one or more buffering agents such as sodium or potassium citrate, sodium phosphate, dibasic sodium phosphate, calcium carbonate, hydrogen phosphate, phosphate, or sulfate, sodium or magnesium carbonate, sodium ascorbate or benzoate, sodium or potassium hydrogen carbonate or lauryl sulfate, or mixtures of such buffering agents.

If required, the formulation may also include surfactants and other conventional components for solid, pharmaceutical formulations such as coloring agents, lakes, aromas and adsorbents. As surfactants the following may be used: ionic surfactants, such as sodium lauryl sulfate or non-ionic surfactants such as different poloxamers (polyoxyethylene and polyoxypropylene copolymers), natural or synthesized lecithins, esters of sorbitan and fatty acids (such as Span®, manufactured by Atlas Chemie), esters of polyoxyethylene-sorbitan and fatty acids (such as Tween®, manufactured by Atlas Chemie), polyoxyethylated hydrogenated castor oil (such as Cremophor®, manufactured by BASF), polyoxyethylene stearates (such as Brij®, manufactured by Atlas Chemie), dimethylpolysiloxane, or any combination of the above mentioned surfactants.

If the pharmaceutical formulation is in the form of coated tablets, the coating may be prepared from at least one film-former such as hydroxypropyl methylcellulose, hydroxypropyl cellulose, at least one plasticizer such as polyethylene glycols, dibutyl sebacate, triethyl citrate, and other pharmaceutical auxiliary substances conventional for film coatings, such as pigments, fillers and others.

The pharmaceutical formulation may be prepared by conventional methods known to those skilled in the art.

The present invention is illustrated but in no way limited by the following examples.

EXAMPLE 1

4.37 g (6.7 mmol) of compound III was dissolved in 200 mL of tetrahydrofuran, 15 mL of 10% HCl was added, and the solution was stirred at room temperature for 15 hours. 3.6 g (90 mmol) of solid NaOH was added to this solution, and the solution stirred for an additional 30 hours. The solution was concentrated by vacuum evaporation to 50 mL. 50 mL of water and 80 mL of hexane were added. The phases were separated, and to the rapidly agitated aqueous phase 5M HCl was added carefully to a pH of 7.0–7.5. The solution was heated to 35° C., and 0.76 g (4.3 mmol) $Ca(OAc)_2 \cdot xH_2O$ in 20 mL preheated to 35° C., was added to the agitated solution. After the completed addition, the solution was stirred for additional 1 hour at room temperature and then placed in a refrigerator for 2 hours. The formed precipitate was filtered, rinsed with water (2×20 mL) and dried at 40° C. for 18 hours to give 3.75 g of non-crystalline atorvastatin calcium.

EXAMPLE 2

3.00 g of compound III was dissolved in 140 mL of tetrahydrofuran, 10 mL of 10% HCl was added, and the solution was stirred at room temperature. 3.6 g of solid NaOH was added to this solution, and the solution was stirred for 30 hours. The solution was concentrated by vacuum evaporation to 20%–25% of its initial volume. Then the same amount of water, and a 1.6-fold amount of hexane, as the volume of the remaining concentrated solution were added. The phases were separated and to the rapidly agitated aqueous phase 5M HCl was added carefully to a pH to 7.0. The solution was heated to 35° C. and 0.76 g $Ca(OAc)_2 \cdot xH_2O$ in 20 mL of water, preheated to 35° C., was added to the agitated solution. After the completed addition, the solution was stirred for an additional 1 hour at room temperature and then placed in a refrigerator for 2 hours. The formed precipitate was filtered, rinsed with water, and dried at 40° C. for 18 hours to give 2.23 g of non-crystalline atorvastatin calcium.

The obtained non-crystalline atorvastatin calcium has the X-ray powder diffractogram substantially that shown in the FIGURE. The X-ray powder diffraction pattern was collected on a Philips PW1710 diffractometer in reflection geometry. The instrument was regularly calibrated with a silicon standard. The sample was not ground before the measurement. A standard Philips back-loading sample holder was used. Sample storage, mounting, and data collection were done at room temperature. Instrumental parameters were: $CuK_\alpha$ radiation (30 mA, 40 kV, $\lambda$=1.5406 Å, variable divergence slit (approx. 12×16 mm irradiated area), 0.4 mm receiving slit, graphite monochromator on the secondary side, scintillation counter. Data collection parameters were: $2\theta$ range from 4° to 37°, step scan mode in steps of 0.04° $2\theta$, integration time 1 second at each step.

We claim:

1. A process for preparing a pharmaceutically acceptable atorvastatin salt in non-crystalline form, which comprises:
    (a) providing a solution of atorvastatin lactone in a non-hydroxylic solvent;
    (b) opening the lactone ring;
    (c) optionally concentrating the solution to not more than half its initial volume;
    (d) adding water to the optionally concentrated solution;
    (e) adding a solvent which is slightly miscible or immiscible with water and in which the pharmaceutically acceptable atorvastatin salt is insoluble or practically insoluble, in an amount not less than the water volume added in step (d);
    (f) optionally mixing the phases, and then separating the two phases;
    (g) neutralizing the aqueous phase;
    (h) converting atorvastatin in the aqueous phase to the pharmaceutically acceptable salt; and
    (i) precipitating the pharmaceutically acceptable atorvastatin salt in non-crystalline form.

2. A process for preparing a pharmaceutical formulation containing a pharmaceutically acceptable atorvastatin salt in non-crystalline form, which comprises:
    (a) preparing a pharmaceutically acceptable atorvastatin salt in non-crystalline form by the process of claim 1; and
    (b) mixing the prepared pharmaceutically acceptable atorvastatin salt in non-crystalline form with a pharmaceutically acceptable carrier.

3. The process of claim 2 wherein the pharmaceutically acceptable salt is a calcium salt.

4. The process of claim 1 wherein the non-hydroxylic solvent is selected from the group consisting of tetrahydrofuran, 1,4-dioxane, acetone, ethyl acetate, a mixture of these solvents, and a mixture of one or more of these solvents with toluene, n-heptane, n-hexane, or acetonitrile in the volume ratio from 1:0.01 to 1:1.0.

5. The process of claim 4 wherein the non-hydroxylic solvent is tetrahydrofuran.

6. The process of claim 1 wherein the solvent, which is slightly miscible or immiscible with water, and in which the pharmaceutically acceptable atorvastatin salt is insoluble or practically insoluble, is selected from the group consisting of hexane, heptane, cyclohexane, ether, and diisopropyl ether.

7. The process of claim 6 wherein the solvent which is slightly miscible or immiscible with water, and in which the pharmaceutically acceptable atorvastatin salt is insoluble or practically insoluble, is hexane.

8. The process of claim 1 wherein the atorvastatin lactone solution of step a) is formed during lactone synthesis.

9. The process of claim 1 wherein step b) comprises adding a base and maintaining the solution at from 40° C. to 60° C.

10. The process of claim 9 wherein the base is an alkali metal hydroxide or alkaline earth metal hydroxide, and the molar ratio of the base to the lactone is from 1:0.2 to 1:0.6.

11. The process of claim 1 wherein step c) comprises concentrating the solution to from 15% to 50% of its initial volume.

12. The process of claim 1 wherein step d) comprises adding water in 0.2-fold to 5-fold relative to the volume of the optionally concentrated solution.

13. The process of claim 12 wherein step d) comprises adding water in 0.6-fold to 1.5-fold relative to the volume of the optionally concentrated solution.

14. The process of claim 1 wherein step e) comprises adding the solvent in 1-fold to 5-fold relative to the water volume previously added in step d).

15. The process of claim 1 wherein step g) comprises adding an acid to the aqueous phase to adjust its pH to from 6.5 to 8.

16. The process of claim 1 wherein step h) comprises heating the neutralized aqueous solution to from 30° C. to 40° C., and then adding a 30° C. to 40° C. aqueous solution of a salt of the pharmaceutically acceptable cation.

17. The process of claim 16 wherein, after the addition of the salt, the solution is mixed at a temperature of from 10° C. to 30° C.

18. The process of claim 1, wherein step i) comprises adjusting the temperature of the solution to from 2° C. to 15° C. to precipitate the pharmaceutically acceptable atorvastatin salt in non-crystalline form.

19. The process of claim 1 wherein step i) comprises adding a water-miscible organic solvent in which the pharmaceutically acceptable atorvastatin salt is insoluble or practically insoluble.

* * * * *